(12) United States Patent
Flanagan et al.

(10) Patent No.: US 8,826,473 B2
(45) Date of Patent: Sep. 9, 2014

(54) MOISTURE DETECTION SYSTEM

(75) Inventors: Joseph Flanagan, Aurora, IN (US); Chris Newport, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 382 days.

(21) Appl. No.: 13/185,751

(22) Filed: Jul. 19, 2011

(65) Prior Publication Data
US 2013/0019405 A1    Jan. 24, 2013

(51) Int. Cl.
*A47B 71/00* (2006.01)
*A61G 7/057* (2006.01)

(52) U.S. Cl.
CPC ...... *A61G 7/057* (2013.01); *A61G 2007/05784* (2013.01); *A61G 2203/30* (2013.01); *A61G 2203/34* (2013.01); *Y10S 5/94* (2013.01); *Y10S 5/904* (2013.01); *Y10S 5/905* (2013.01)
USPC ............. 5/600; 5/484; 5/487; 5/940; 5/904; 5/905

(58) Field of Classification Search
CPC ...... A61G 7/057; A47C 21/04; A47C 21/042; A47C 21/044
USPC ............. 5/484, 487, 940, 904, 905, 600; 340/573.1
See application file for complete search history.

(56) References Cited

U.S. PATENT DOCUMENTS

| | | | |
|---|---|---|---|
| 5,144,284 A * | 9/1992 | Hammett | 340/573.1 |
| 5,265,296 A * | 11/1993 | Abbas et al. | 5/612 |
| 5,438,721 A * | 8/1995 | Pahno et al. | 5/604 |
| 5,771,511 A | 6/1998 | Kummer et al. | |
| 6,948,205 B2 * | 9/2005 | Van Der Wurf et al. | 5/718 |
| 7,176,419 B2 * | 2/2007 | Ellis et al. | 219/528 |
| 7,237,287 B2 | 7/2007 | Weismiller et al. | |
| 7,506,390 B2 | 3/2009 | Dixon et al. | |
| 7,520,006 B2 | 4/2009 | Menkedick et al. | |
| 7,568,246 B2 | 8/2009 | Weismiller et al. | |

(Continued)

FOREIGN PATENT DOCUMENTS

WO     2011117862 A2     9/2011

OTHER PUBLICATIONS

Nite Train-R; Wet Call Bed-Side Bed Wetting Alarm with Pad, www. Amazon.com, Health & Personal Care.
Textile Moisture Sensor Matrix for Monitoring of Disabled and Bed-Rest Patients publication; Tiago Pereira, Pedro Silva—Dep. Industrial Electronics, University of Minho, Guimarales, Portugal; Helder Cavalho, Miguel Cavalho—Dep.Textile Engineering, University of Minho, Guimarales, Portugal; Acknowledgement to FCT, project PTD/SAU-BEB/68678/2006.

(Continued)

*Primary Examiner* — Robert G Santos
*Assistant Examiner* — David E Sosnowski
(74) *Attorney, Agent, or Firm* — Kenneth C. Baran (57) ABSTRACT

A moisture detection and alarming system connected to a person-support apparatus has been described. The system comprises a moisture detection sheet connected to at least one pressure sensor, at least moisture sensor and a controller. The pressure sensor can be configured to send a signal to the controller. The controller can be configured to receive the pressure signal from the pressure sensor and determine the presence of a person supported on the person support apparatus. If a person is supported on the person-support apparatus then a moisture sensor is activated by the controller to sense the moisture content on a mattress pad. If the moisture content on the mattress pad is out of a predefined range then an alarming unit can be activated. The controller may further be connected to at least one of a hospital network, communication station and nurse call system.

13 Claims, 6 Drawing Sheets

(56) References Cited

U.S. PATENT DOCUMENTS

| | | | |
|---|---|---|---|
| 8,181,290 B2* | 5/2012 | Brykalski et al. | 5/423 |
| 8,191,187 B2* | 6/2012 | Brykalski et al. | 5/423 |
| 8,332,975 B2* | 12/2012 | Brykalski et al. | 5/421 |
| 8,525,679 B2* | 9/2013 | Riley et al. | 340/573.1 |
| 2008/0263776 A1* | 10/2008 | O'Reagan et al. | 5/714 |
| 2010/0043143 A1* | 2/2010 | O'Reagan et al. | 5/421 |
| 2011/0068939 A1* | 3/2011 | Lachenbruch | 340/626 |
| 2011/0092890 A1* | 4/2011 | Stryker et al. | 604/23 |
| 2011/0115635 A1* | 5/2011 | Petrovski et al. | 340/584 |
| 2011/0283459 A1* | 11/2011 | Essers | 5/699 |
| 2011/0302720 A1* | 12/2011 | Yakam et al. | 5/710 |
| 2013/0019406 A1* | 1/2013 | Riley et al. | 5/600 |

OTHER PUBLICATIONS

Fabric Selection for Textile Moisture Sensor Design publication; Material Science, Textile and Clothing Technology; Jul. 2012; Inese Parkova, Inese Ziemele, Ausma Vilumsone, Riga Technical University.

Electrical Characterization of a Textile Sensor for Moisture Detection; Final Degree Thesis 15 ECTS, Nov. 2010 Sweden; Thesis No. Jan. 2011, Biomedical Engineering; Arun Swaminathan, Muhammad Babar Khan; Hogskolan I Boras, Institutionen Ingenjorshogskolan.

* cited by examiner

MOISTURE DETECTION SYSTEM

BACKGROUND OF THE DISCLOSURE

This disclosure relates to a moisture detection system. More particularly, but not exclusively, one illustrative embodiment relates to a moisture detection and alarming system to be used with a person-support apparatus.

Circumstances may cause the patient to remain confined to a bed for a prolonged period of time, in many instances, for periods greater than a week. Confinement on a bed for continuous and extended time periods may result in accumulation of excessive moisture due to sweating while in contact with the bed. Bed wetting may also be one of the sources of additional of moisture content between the patient body surface and the bed. Presence of excessive moisture for prolonged periods can be very harmful as the patient is susceptible to diseases like skin erosion, fungal infection, pressure ulcer or bed sores. While various moisture sensing devices have been developed, there is still room for improvement. Thus, a need persists for further contributions in this area of technology.

SUMMARY OF THE DISCLOSURE

The present disclosure includes one or more of the features recited in the appended claims and/or the following features which, alone or in any combination, may comprise patentable subject matter.

One illustrative embodiment of the current disclosure of a moisture detection system includes a person-support surface comprising a ticking layer and a core layer. The moisture detection system may further comprise a moisture detection sheet mounted external to the outer surface of the ticking layer in a removable manner. At least one moisture sensor and one pressure sensor may be connected to the moisture detection sheet in this embodiment and in communication with a controller. The controller may further be connected to a hospital communications network.

Another illustrative embodiment of the current disclosure of a moisture detection system includes a person-support surface comprising a ticking layer and a core layer. The moisture detection system may further comprise a moisture detection sheet between the ticking layer and the core layer. At least one moisture sensor and one pressure sensor may be connected to the moisture detection sheet in this embodiment and in communication with a controller. The controller may further be connected to a hospital communications network.

Another illustrative embodiment of the current disclosure of a moisture detection system includes a person-support surface comprising a ticking layer and a core layer. The moisture detection system may further comprise a moisture detection sheet mounted either external to the ticking layer or between the ticking layer and the core layer. At least one moisture sensor may be connected to the moisture detection sheet in this embodiment and in communication with a controller. A pre-existing pressure sensor mounted on any one of the person-support structure, person-support surface or any other device may be connected to the controller in this embodiment. The controller may further be connected to a hospital communications network Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout.

DESCRIPTION OF SPECIFIC ILLUSTRATIVE EMBODIMENTS

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

Figure 1:
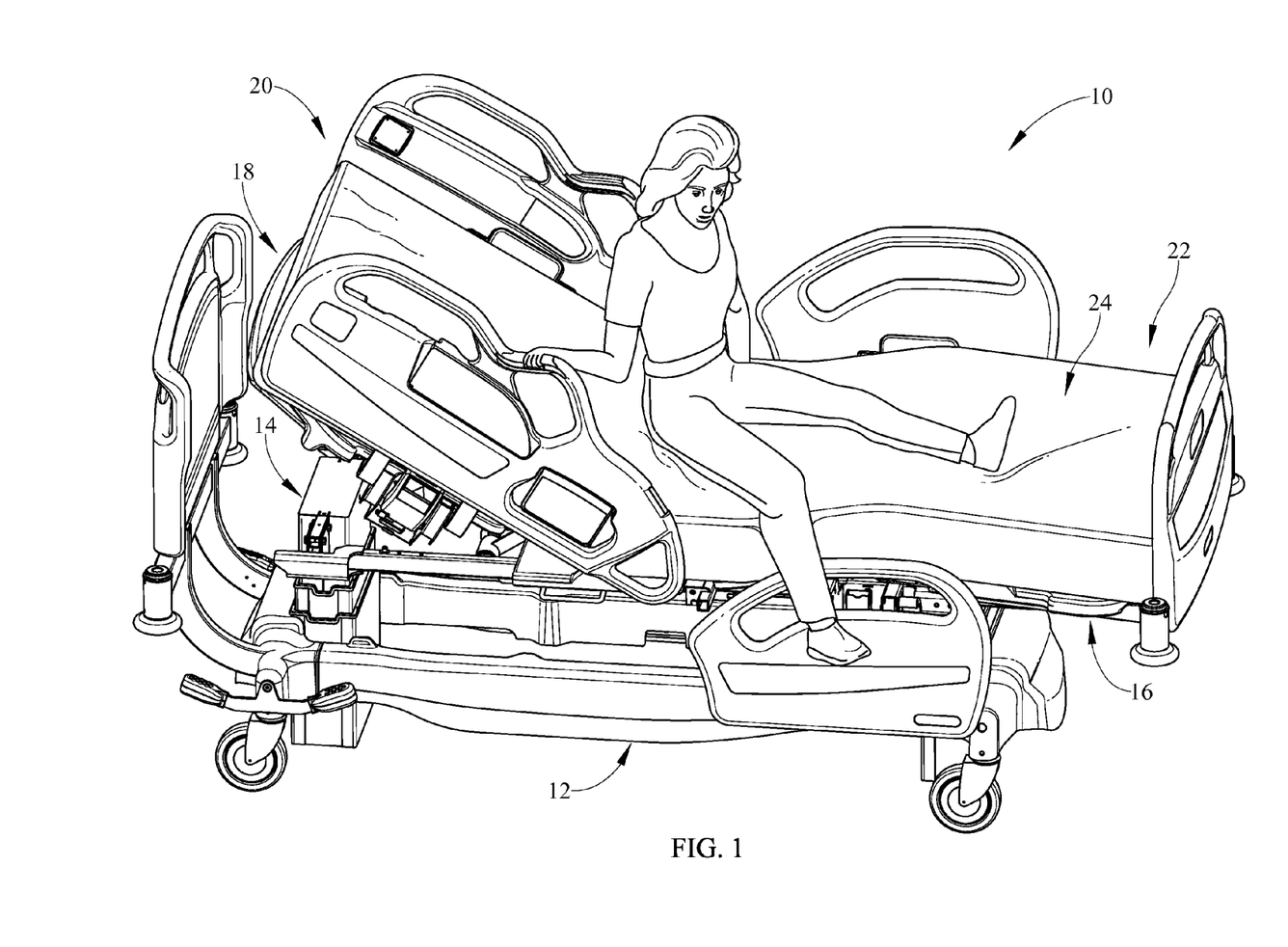
FIG. 1 is a perspective view of a person-support apparatus equipped with a moisture detection system.

A person-support apparatus 10 according to one illustrative embodiment of the current disclosure is shown in FIG. 1. In one embodiment, the person-support apparatus 10 can be a hospital bed. It should be appreciated that the person-support apparatus 10 can also be a hospital stretcher or an operating table. The person-support apparatus 10 can include a lower frame 12 or base 12, a plurality of supports 14 coupled with the lower frame 12, and an upper frame 16 supported on the plurality of supports 14 above the lower frame 12. The person-support apparatus 10 can also include a deck 18 supported on the upper frame 16. The deck 18 of the person-support apparatus 10 can include a head support section 20 supporting head of the person and a foot support section 22 supporting feet of the person. The deck 18 can further support a person support surface 24 or a mattress 24 as shown in FIG. 1.

Figure 2:
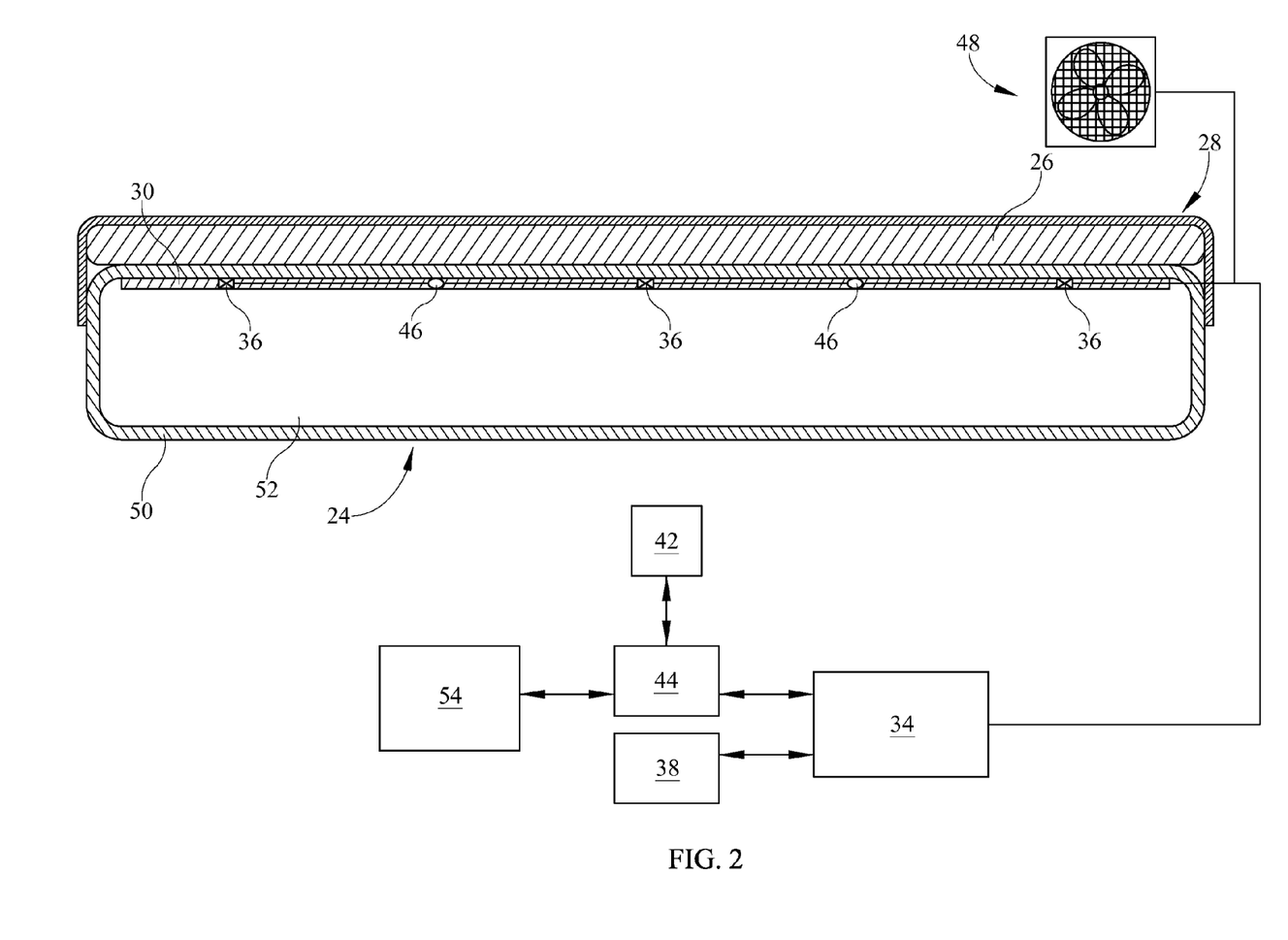
FIG. 2 is a cross-sectional side view of a person-support surface along with an embodiment of the claimed subject matter wherein the moisture detection sheet is located between the ticking layer and the core layer.

The claimed subject matter as shown in FIG. 2 describes a moisture detection system with a person-support surface 24. The person-support surface 24 comprises an outer ticking layer 50 and an inner core layer 52. In one embodiment of the claimed subject matter as shown in FIG. 2, a moisture detection sheet 30 may be included in between the ticking layer 50 and the core layer 52. One skilled in the art would appreciate that the moisture detection sheet 30 may be made of any material, including but not limited to organic and inorganic fabrics, manmade materials and combinations thereof. The moisture detection sheet 30 may be of any size and thickness. The moisture detection sheet 30 has at least one moisture sensor 36 and at least one pressure sensor 46 connected to it. One skilled in the art would appreciate that one or a combination of devices may be used as the moisture sensor 36. These include, but are not limited to capacitive, resistive and thermally conductive sensors. One skilled in the art would appreciate that in one embodiment of the claimed subject matter, fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment fibers of the moisture detection sheet 30 may serve as pressure sensors. The moisture sensor 36 and pressure sensor 46 convey electrical signals to a controller 34. The controller 34 is in communication with a hospital network 44. One skilled in the art would appreciate that the communication between the controller 34 and the hospital network 44 may be through a wired connection or a wireless connection. Wired communication may include communication via the telephone line, Ethernet network, cable and fiber optic cables. Wireless communication may include communication via radio frequency, microwave and infrared (IR) modalities. The hospital network 44 may further be connected to any one or both of a communication station 54 and a nurse call system 42. These connections may also be of a wired or wireless nature as described above. Selective or all of the information from the controller 34 may be transmitted to the communication station 54 and the nurse call system 42. Controller 34 may be communication with an air blower assembly 48 placed external to the outer surface of the ticking layer of the person-support surface 24. The controller 34 provides a signal to the air blower assembly to initiate blowing air. The controller 34 can be electrically coupled to at least one moisture sensor 36 and at least one pressure sensor 46 with the help of wires 40. It should be appreciated that the controller 34 can also be coupled through wireless communication. The controller 34 can be any programmable device configured to receive signals from at least one moisture sensor 36 and send a signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. Although the following elements are not necessary for operation of the claimed subject matter, one skilled in the art would appreciate that several layers may be placed on top of the person-support surface, including, but not limited to a mattress pad 26 and mattress cover 28. One skilled in the art would appreciate that in an embodiment where more than one additional layer has been included with the person-support surface 24, the air blower assembly 48 may be configured to blow air in any combination external to all the layers or between layers.

Figure 3:
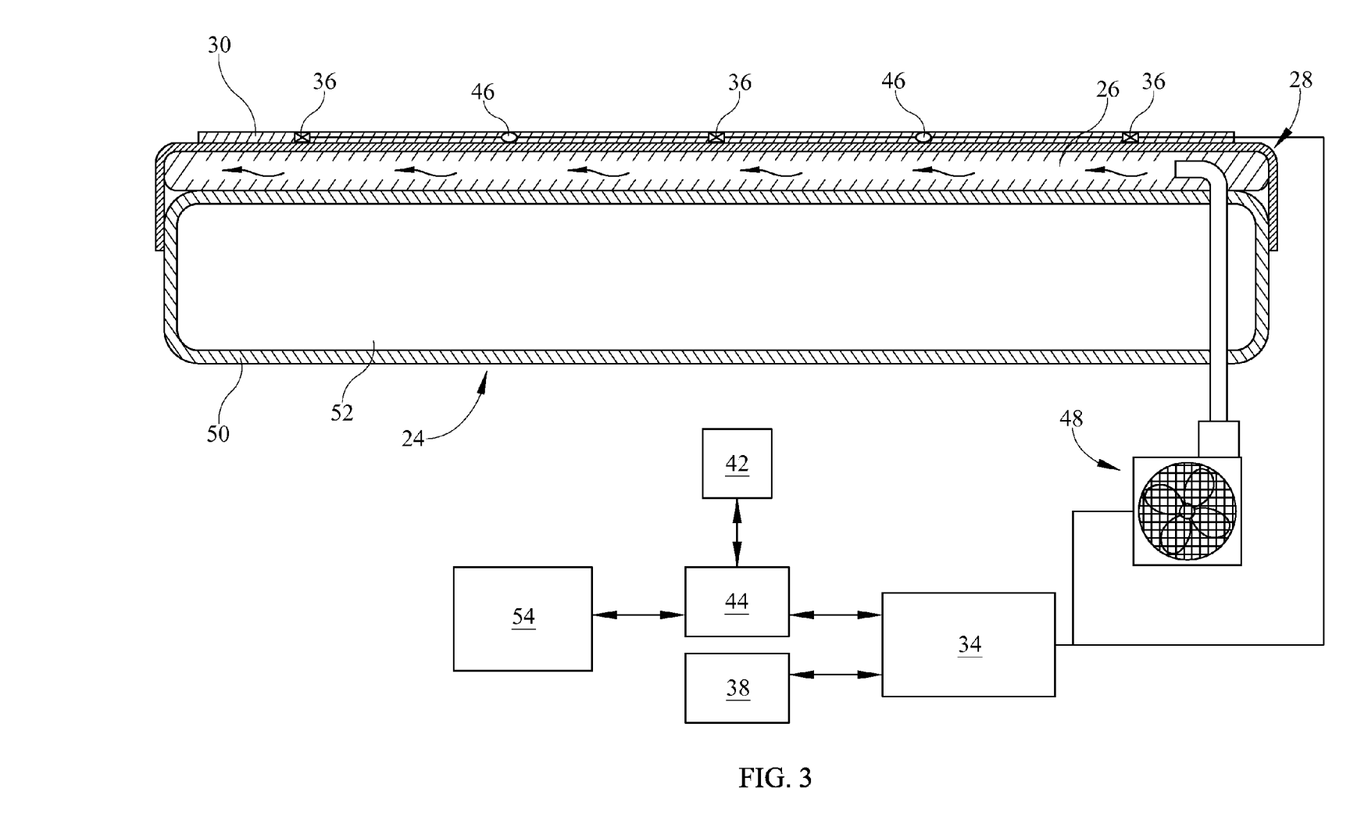
FIG. 3 is a cross-sectional side view of a person-support surface along with an embodiment of the claimed subject matter wherein the moisture detection sheet is located external to the ticking layer.

The claimed subject matter as shown in FIG. 3 describes a moisture detection system with a person-support surface 24. The person-support surface 24 comprises an outer ticking layer 50 and an inner core layer 52. In one embodiment of the claimed subject matter as shown in FIG. 3, a moisture detection sheet 30 may be included external to the person-support surface. Although the following elements are not necessary for operation of the claimed subject matter, one skilled in the art would appreciate that several layers may be placed on top of the person-support surface, including, but not limited to a mattress pad 26 and mattress cover 28. One skilled in the art would appreciate that in an embodiment where more than one additional layer has been included with the person-support surface 24, the moisture detection sheet 30 may be may be placed external to all the layers or between layers. Further, one skilled in the art would appreciate that the moisture detection sheet may simply be placed on top of or between layers or may be integral to any additional layer. Some of the types of connections locating the moisture detection sheet 30 on any other surface may include, but, are not limited to zippered connection, stitched connection, Velcro connection, hooked connection or a buttoned connection. One skilled in the art would appreciate that the moisture detection sheet 30 may be made of any material, including but not limited to organic and inorganic fabrics, manmade materials and combinations thereof. The moisture detection sheet may be of any size and thickness. The moisture detection sheet has at least one moisture sensor 36 and at least one pressure sensor 46 connected to it. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment, fibers of the moisture detection sheet 30 may serve as pressure sensors. The moisture sensor 36 and pressure sensor 46 convey electrical signals to a controller 34. The controller 34 is in communication with a hospital network 44. One skilled in the art would appreciate that the communication between the controller 34 and the hospital network 44 may be through a wired connection or a wireless connection. Wired communication may include communication via the telephone line, Ethernet network, cable and fiber optic cables. Wireless communication may include communication via radio frequency, microwave and infrared (IR) modalities. The hospital network 44 may further be connected to any one or both of a communication station 54 and a nurse call system 42. These connections may also be of a wired or wireless nature as described above. Selective or all of the information from the controller 34 may be transmitted to the communication station 54 and the nurse call system 42. Controller 34 may be in communication with an air blower assembly 48 placed external to the outer surface of the ticking layer of the person-support surface 24. The controller 34 provides a signal to the air blower assembly 48 to initiate blowing air. The controller 34 can be electrically coupled to at least one moisture sensor 36 and at least one pressure sensor 46 with the help of wires 40. It should be appreciated that the controller 34 can also be coupled through wireless communication. The controller 34 can be any programmable device configured to receive signals from at least one moisture sensor 36 and send the signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. One skilled in the art would appreciate that in an embodiment where more than one additional layer has been included with the person-support surface 24, the air blower assembly 48 may be configured to blow air in any combination external to all the layers or between layers.

Figure 4:
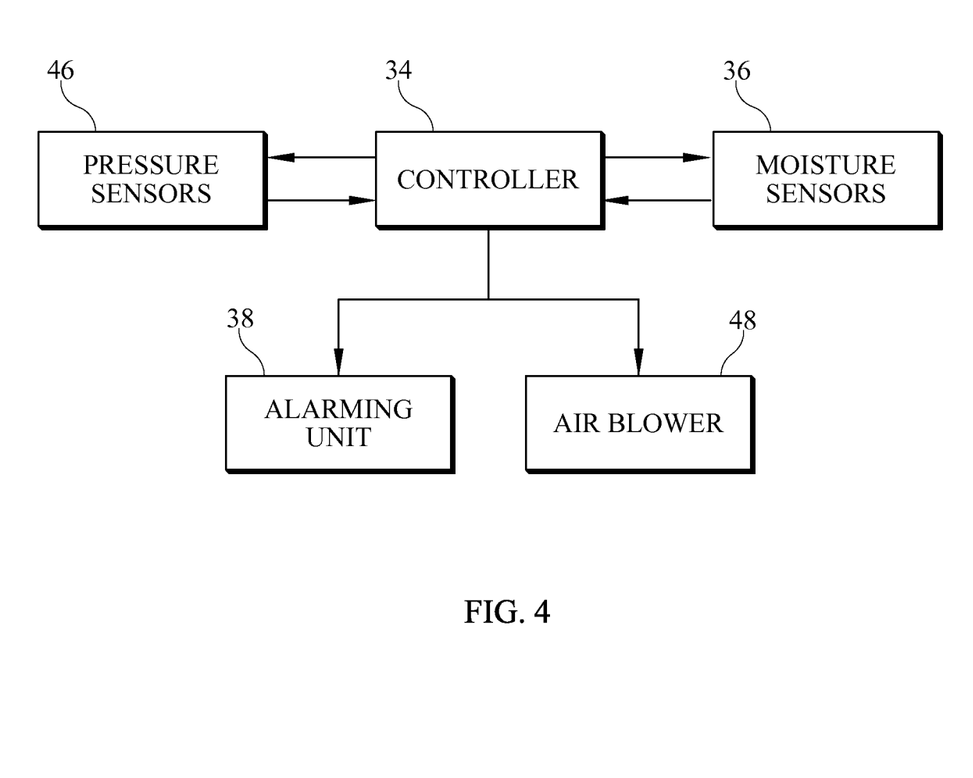
FIG. 4 is a block diagram showing various components and connection of the moisture detection system.

The claimed subject matter as shown in FIG. 4 shows the connections between some of the electro-mechanical, sensing and control elements. The controller 34 is connected to at least one moisture sensor 36 and may further be connected to at least one pressure sensor 46. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment fibers of the moisture detection sheet 30 may serve as pressure sensors. In one embodiment, the pressure sensor 46 may be connected to the moisture detection sheet 30. In another embodiment, the pressure sensor 46 may be mounted on any part of the person-support apparatus 10, person-support surface 24 or any additional layers that may be placed on top of the person-support surface 24. The controller 34 can be any programmable device configured to send a signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. Although not shown in FIG. 4, in one embodiment of the claimed subject matter, the controller 34 may be further connected to a hospital network 44, which may in turn be connected to at least one of a nurse call system 42 and a communication station 54. Although not shown in FIG. 4, in another embodiment of the claimed subject matter, the alarming unit 38 may be connected to the hospital network 44. Controller 34 as shown in FIG. 4 is in communication with an air blower assembly 48. Controller 34 provides a signal to the air blower assembly 48 to initiate blowing air. In one embodiment of the claimed subject matter, the air blower assembly 48 may include a timing mechanism which may shut off the air blower assembly 48 automatically after a predetermined period of time. In another embodiment of the claimed subject matter as shown in FIG. 4, the controller 34 may provide a signal to the air blower assembly 48 to stop blowing air. In yet another embodiment, the air blower assembly 48 may include a variety of preprogrammed regimes to blow air at a variety of speeds. In yet another embodiment, although not shown in FIG. 4, the air blower assembly 48 may include a heater element to heat the air.

Figure 5:
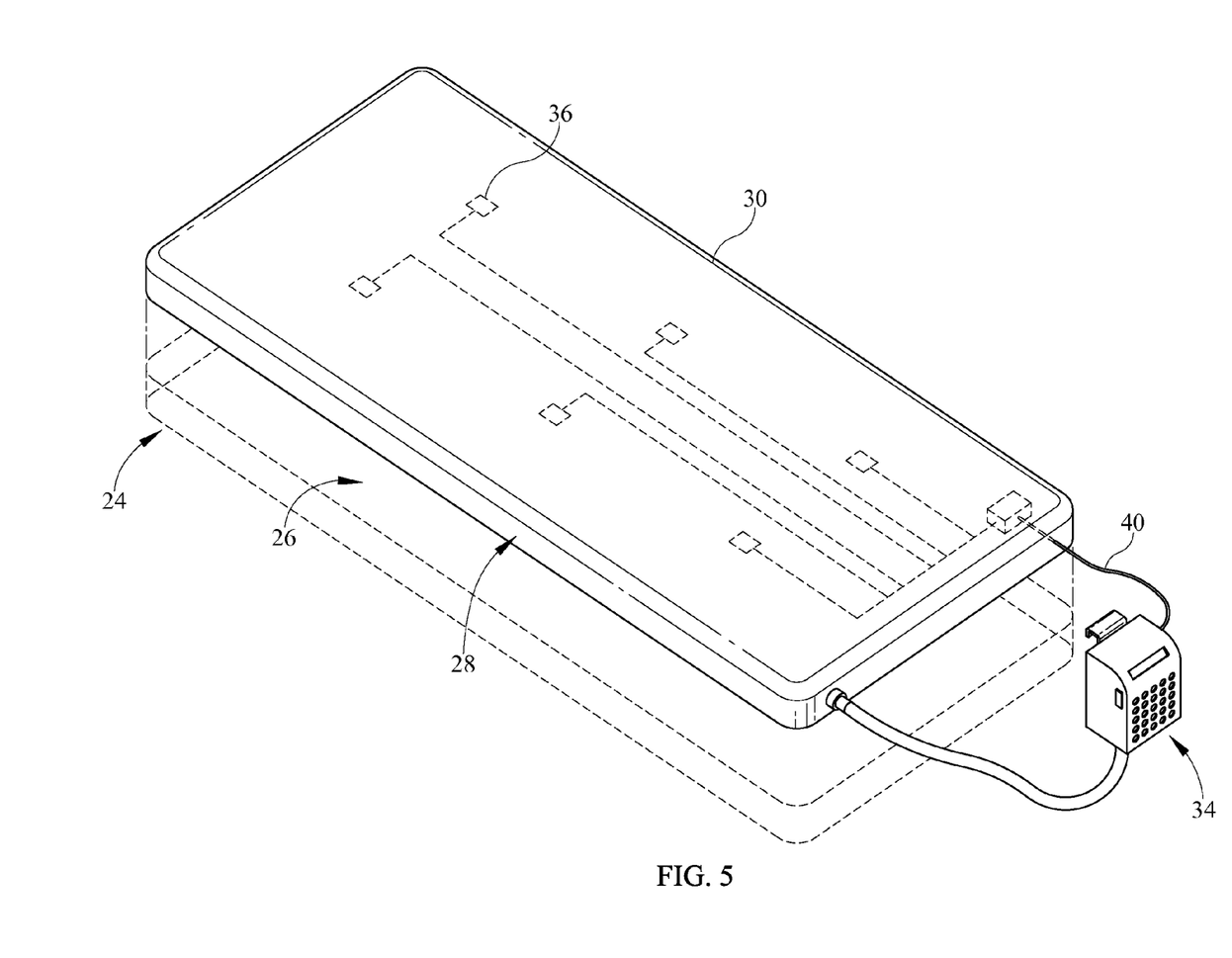
FIG. 5 is a perspective view of the person support surface along with the moisture detection system.

The claimed subject matter as shown in FIG. 5 shows a moisture detection sheet 30 configured to mount on top of a mattress cover 28. One skilled in the art would appreciate that the moisture detection sheet 30 may be placed between any of the layers added on top of the person-support surface 24 or may be placed between the ticking layer 50 and core layer 52 of the patient support surface 24. The moisture detection sheet 30 has at least one moisture sensor 36 connected to it. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. A controller 34 can be electrically coupled to at least one moisture sensor 36 with the help of wires 40. It should be appreciated that the controller 34 can also be coupled through wireless communication. The controller 34 can be any programmable device configured to receive signals from at least one moisture sensor 36. In the embodiment shown in FIG. 5, an air blower assembly 48 is integral to the controller 34. The air blower assembly blows air between the mattress cover and the mattress pad as shown in FIG. 5. In another embodiment the air blower assembly may blow air between any of the layers added on top of the person-support surface 24 or between the ticking layer 50 and core layer 52 of the patient support surface 24. Although not shown in FIG. 5, at least one pressure sensor embedded in or connected to any portion of the person-support apparatus 10 provides a signal to the controller 34. In one embodiment of the claimed subject matter shown in FIG. 5, integral to the controller 34 is an alarming unit 38. The alarming unit 38 can be at least one of an audio alarm, video alarm, vibration alarm or any other mode. It should also be appreciated that the alarming unit 38 can also include a pre-alarming feature. In another embodiment, the alarming unit 38 may be a separate system connected to the controller 34.

Figure 6:
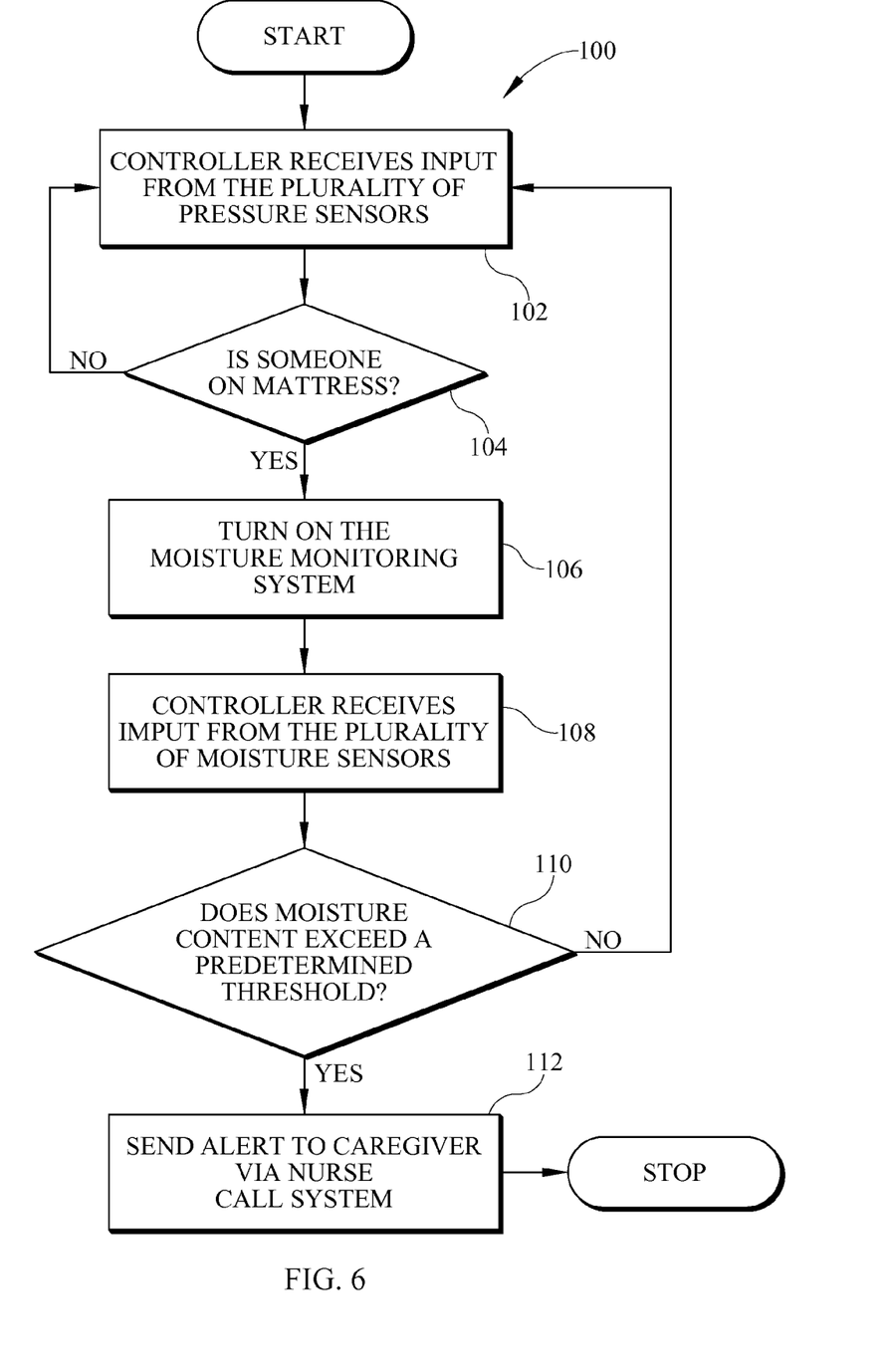
FIG. 6 is a flowchart showing various steps involved in the operation of the moisture detection system.

The claimed subject matter as shown in FIG. 6 shows the operation of one embodiment of the claimed subject matter via a flowchart 100. At step 102, the controller 34 can be configured to receive input from at least one pressure sensor 46. At step 104, the controller 34 can determine the presence of the person on the person-support apparatus 10 by comparing the signal received from the at least one pressure sensor 46 against a predetermined value. If the input from the at least one pressure sensor 46 is above a predetermined value, the controller will activate at least one moisture sensor 36 at step 106. At step 108, controller 34 can be configured to receive input from at least one moisture sensors 36. At step 110 the controller 34 compares the signal received from at least one moisture sensor with a predetermined range of values. At step 112, if the moisture content is more than the predefined range then the controller 34 can send an alert to the alarming unit 38. In another embodiment, at step 112 if the moisture content is more than the predefined range, then the controller sends a signal to the hospital network 44. Although not shown in the FIG. 6, comparison of signals from at least one pressure sensor against another predetermined value may be allow for an alert for a potential patient bed fall. In this case, the controller 34 can send an alert to the alarming unit 38 or the hospital network 44.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless need not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A moisture detection system for use on a hospital bed comprising:
    a person-support surface comprising a ticking layer and a core layer, said ticking layer comprising an inner surface and an outer surface, said inner surface facing said core layer;
    a moisture detection sheet located between said ticking layer and said core layer;
    at least one moisture sensor connected to said moisture detection sheet;
    at least one pressure sensor connected to said moisture detection sheet;
    a controller in communication with at least one of said at least one pressure sensor and said at least one moisture detection sensor.

2. The moisture detection system of claim 1, said controller configured to trigger an alarm unit in response to communication from at least one of said at least one pressure sensor and said at least one moisture sensor exceeding a predetermined threshold, said alarming unit configured to provide at least one of an audible sound, light signal and vibrations.

3. The moisture detection system of claim 1, further comprising a blower configured to blow air external to said outer surface, said blower in communication with said controller.

4. The moisture detection system of claim 3, said blower configured to blow air upon communication from said controller.

5. The moisture detection system of claim 4, said controller configured to communicate with said blower in response to communication from said at least one moisture sensor exceeding a predetermined threshold.

6. The moisture detection system of claim 1, further comprising a blower configured to blow air in between said ticking layer and said core layer, said blower in communication with said controller.

7. The moisture detection system of claim 6, said blower configured to blow air upon communication from said controller.

8. The moisture detection system of claim 7, said controller configured to communicate with said blower in response to communication from said at least one moisture sensor exceeding a predetermined threshold.

9. The moisture detection system of claim 1, further comprising a hospital communication network.

10. The moisture detection system of claim 9, communication between said controller and said hospital communication network is wireless.

11. The moisture detection system of claim 9, said hospital communication network including at least one of a nurse call alert and a communication station.

12. The system of claim 1 wherein the controller is a programmable device.

13. The system of claim 1 wherein:
    the controller is configured to receive input from at least one of the pressure sensors and to activate at least one of the moisture sensors if the input from the pressure sensor is above a predetermined value.

* * * * *